United States Patent
Edney et al.

(10) Patent No.: US 10,379,125 B2
(45) Date of Patent: Aug. 13, 2019

(54) SYSTEM AND METHOD FOR DYNAMICALLY CALIBRATING AND MEASURING ANALYTE CONCENTRATION IN DIABETES MANAGEMENT MONITORS

(71) Applicant: Becton, Dickinson and Company, Franklin Lakes, NJ (US)

(72) Inventors: Paul Edney, Amesbury, MA (US); Ling Zheng, Acton, MA (US); James Petisce, Westford, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/448,867

(22) Filed: Jul. 31, 2014

(65) Prior Publication Data

US 2015/0185225 A1   Jul. 2, 2015

Related U.S. Application Data

(60) Provisional application No. 61/921,309, filed on Dec. 27, 2013.

(51) Int. Cl.
   *G01N 33/66* (2006.01)
   *A61B 5/145* (2006.01)
   (Continued)

(52) U.S. Cl.
   CPC ........... *G01N 33/66* (2013.01); *A61B 5/0071* (2013.01); *A61B 5/1455* (2013.01);
   (Continued)

(58) Field of Classification Search
   CPC ........ A61M 5/1723; A61M 2205/3507; A61M 5/14244; A61M 5/14276; G01N 33/66;
   (Continued)

(56) References Cited

U.S. PATENT DOCUMENTS

| | | | |
|---|---|---|---|
| 5,094,958 | A | 3/1992 | Klainer et al. |
| 5,319,209 | A | 6/1994 | Miyakawa et al. |

(Continued)

FOREIGN PATENT DOCUMENTS

| | | | |
|---|---|---|---|
| JP | 6500390 | A | 1/1994 |
| JP | 06082459 | A | 3/1994 |

(Continued)

OTHER PUBLICATIONS

Enson et al. In vivo studies with an intravascular and intracardiac reflection oximeter. J Appl Physiol, (17):552-558, 1962.

(Continued)

*Primary Examiner* — Dean Kwak
(74) *Attorney, Agent, or Firm* — Dickinson Wright, PLLC (57) ABSTRACT

An optical analyte sensor and diabetes management system is provided. The sensor preferably includes a hydrogel matrix for receiving a sample containing an analyte at unknown concentration, a light emitter for emitting light at a stimulation frequency, a light receiver for receiving a fluorescence signal at a first isosbestic frequency, and at a second frequency, for measuring an intensity of the fluorescence signal and the first and second frequencies. A processor determines a concentration of the analyte based on the respective intensities.

7 Claims, 5 Drawing Sheets

(51) Int. Cl.
*A61B 5/1495* (2006.01)
*A61B 5/00* (2006.01)
*A61B 5/1459* (2006.01)
*A61M 5/172* (2006.01)
*A61B 5/1455* (2006.01)

(52) U.S. Cl.
CPC .......... *A61B 5/1459* (2013.01); *A61B 5/1495* (2013.01); *A61B 5/14532* (2013.01); *A61M 5/1723* (2013.01); *A61B 5/14507* (2013.01); *A61B 5/4839* (2013.01); *A61B 2560/0223* (2013.01)

(58) Field of Classification Search
CPC .. A61B 5/14532; A61B 5/4839; A61B 5/0071
USPC ....... 600/316, 310; 422/82.05, 108; 436/172
See application file for complete search history.

(56) References Cited

U.S. PATENT DOCUMENTS

| | | | |
|---|---|---|---|
| 5,409,835 A | 4/1995 | Lakowicz et al. | |
| 5,605,152 A | 2/1997 | Slate et al. | |
| 5,624,847 A | 4/1997 | Lakowicz et al. | |
| 5,628,310 A | 5/1997 | Rao et al. | |
| 6,122,536 A * | 9/2000 | Sun et al. | 600/341 |
| 6,162,611 A | 12/2000 | Heller et al. | |
| 6,163,714 A | 12/2000 | Stanley et al. | |
| 6,168,957 B1 | 1/2001 | Matzinger et al. | |
| 6,275,717 B1 | 8/2001 | Gross et al. | |
| 6,330,464 B1 * | 12/2001 | Colvin, Jr. | A61B 5/0031 128/903 |
| 6,424,847 B1 | 7/2002 | Mastrototaro et al. | |
| 6,514,718 B2 | 2/2003 | Heller et al. | |
| 6,520,326 B2 | 2/2003 | Mcivor et al. | |
| 6,521,446 B2 | 2/2003 | Hellinga | |
| 6,528,809 B1 | 3/2003 | Thomas | |
| 6,546,269 B1 | 4/2003 | Kumik | |
| 6,551,494 B1 | 4/2003 | Heller et al. | |
| 6,560,471 B1 | 5/2003 | Heller et al. | |
| 6,565,509 B1 | 5/2003 | Say et al. | |
| 6,579,690 B1 | 6/2003 | Bonnecaze et al. | |
| 6,585,707 B2 | 7/2003 | Cabiri et al. | |
| 6,615,151 B1 | 9/2003 | Scecina et al. | |
| 6,653,091 B1 | 11/2003 | Dunn et al. | |
| 6,766,183 B2 | 7/2004 | Walsh et al. | |
| 6,780,645 B2 | 8/2004 | Hayter et al. | |
| 6,855,556 B2 | 2/2005 | Amiss et al. | |
| 6,862,465 B2 * | 3/2005 | Shults et al. | 600/347 |
| 7,003,341 B2 | 2/2006 | Say et al. | |
| 7,064,103 B2 | 6/2006 | Pitner et al. | |
| 7,190,988 B2 | 3/2007 | Say et al. | |
| 7,236,812 B1 * | 6/2007 | Ballerstadt et al. | 600/316 |
| 7,316,909 B2 | 1/2008 | Pitner et al. | |
| 7,326,538 B2 | 2/2008 | Pitner et al. | |
| 7,496,392 B2 | 2/2009 | Alarcon et al. | |
| 7,629,172 B2 | 12/2009 | Alarcon et al. | |
| 7,749,729 B2 | 7/2010 | Heinecke et al. | |
| 7,851,593 B2 | 12/2010 | Hsieh et al. | |
| 8,465,981 B2 | 6/2013 | Daunert et al. | |
| 8,467,843 B2 | 6/2013 | Markle et al. | |
| 8,470,300 B2 | 6/2013 | Clark et al. | |
| 8,509,867 B2 | 8/2013 | Workman et al. | |
| 8,741,591 B2 | 6/2014 | Ye et al. | |
| 8,772,047 B2 | 7/2014 | Thomas et al. | |
| 2002/0151772 A1 * | 10/2002 | Polak | A61B 5/14532 600/310 |
| 2003/0153821 A1 | 8/2003 | Berner et al. | |
| 2003/0211454 A1 | 11/2003 | Thomas et al. | |
| 2004/0087842 A1 | 5/2004 | Lakowicz et al. | |
| 2004/0118681 A1 | 6/2004 | Hellinga et al. | |
| 2005/0118726 A1 | 6/2005 | Schultz et al. | |
| 2007/0281368 A1 | 12/2007 | Hsieh et al. | |
| 2008/0275318 A1 | 11/2008 | Lastovich et al. | |
| 2009/0018418 A1 | 1/2009 | Markle et al. | |
| 2009/0104714 A1 | 4/2009 | Thomas et al. | |
| 2011/0184259 A1 | 7/2011 | Alarcon et al. | |
| 2011/0262363 A1 | 10/2011 | Srivastava et al. | |
| 2012/0165636 A1 * | 6/2012 | Feldman et al. | 600/347 |
| 2012/0232251 A1 | 9/2012 | Pickup et al. | |
| 2012/0252046 A1 * | 10/2012 | Fei | A61B 5/145 435/14 |
| 2012/0258467 A1 * | 10/2012 | Chinnayelka | A61B 5/1451 435/7.1 |
| 2013/0060105 A1 | 3/2013 | Shah et al. | |
| 2013/0060106 A1 * | 3/2013 | Aasmul | A61B 5/6849 600/316 |
| 2013/0211212 A1 * | 8/2013 | Stumber | A61B 5/14532 600/316 |
| 2013/0280797 A1 * | 10/2013 | Rao | C12M 47/12 435/288.7 |

FOREIGN PATENT DOCUMENTS

| | | |
|---|---|---|
| JP | 11508792 A | 8/1999 |
| JP | 2000019172 A | 1/2000 |
| JP | 2010526599 A | 5/2010 |
| JP | 2013514809 A | 5/2013 |
| WO | 2008042625 A2 | 4/2008 |

OTHER PUBLICATIONS

Grant et al. A sol-gel based fiber optic sensor for local blood ph measurements. Sensors and Actuators, B(45):35-42, 1997.
Koronczi et al. Development of a submicron optochemical potassium sensor with enhanced stability due to internal reference. Sensors and Actuators, B(51):188-195, 1998.
De Lorimier et al. Construction of a fluorescent biosensor family. Protein Science, (11):2655-2675, 2002.
Malchoff et al. A Novel Noninvasive Blood Glucose Monitor. Diabetes Care 25:2268-2275, 2002.
Khan et al. Fluorescence intensity- and lifetime-based glucose sensing using an engineered high-Kd mutant of glucose/galactose-binding protein. Analytical Biochemistry 399 (2010) 39-43.
Weidemaier et al. Multi-day pre-clinical demonstration of glucose/galactose binding protein-based fiber optic sensor. Biosensors and Bioelectronics, (26):4117-4123, 2011.
Pickup et al. Fluorescence intensity- and lifetime-based glucose sensing using glucose/galactose-binding protein. J Diabetes Sci Technol, 7(1):62-71, Jan. 2013.

* cited by examiner

SYSTEM AND METHOD FOR DYNAMICALLY CALIBRATING AND MEASURING ANALYTE CONCENTRATION IN DIABETES MANAGEMENT MONITORS

This application claims priority under 35 U.S.C. § 119(e) to provisional application No. 61/921,309, filed Dec. 27, 2013, the entire contents of which are hereby incorporated by reference.

FIELD OF THE INVENTION

The present invention relates to systems and methods for monitoring analytes. More particularly, the present invention relates to systems and methods for dynamically calibrating and measuring analyte concentration in diabetes management systems, such as continuous glucose monitors using a fluorescence signal at an analyte concentration independent wavelength. This application claims priority under 35 U.S.C. § 119(e) to provisional application number 61/921,309, filed Dec. 27, 2013, the entire contents of which are hereby incorporated by reference.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications. Chronic hyperglycemia leads to serious sometimes irreversible complications including renal failure, peripheral neuropathy, retinopathy, and vascular system complications.

Treatment options for people with diabetes include specialized diets, oral medications and/or insulin therapy. The primary goal for diabetes treatment is to control the patient's blood glucose (sugar) level in order to increase the chances of a complication-free life.

Glycemic control of patients afflicted with Type 1 or Type 2 diabetes mellitus is essential to minimize acute and chronic effects of hypoglycemia or hyperglycemia. Utilization of continuous glucose monitoring (CGM) as a means to measure effectiveness of treatments focuses on attaining glycemic control was first introduced into commercial use over ten years ago. Since that time, CGM's have been incorporated into insulin pumps which automatically infuse insulin when blood sugar levels are measured by the CGM to be above threshold levels chosen by the patient after consultation with their physician.

Glucose sensors are an essential element in diabetes management. In particular, continuous glucose sensors provide numerous advantages over episodic glucose sensors or conventional finger-stick glucose test strips. Artificial pancreas architectures rely on accurate continuous glucose measurements.

Many existing CGM's are presently based on glucose oxidase. More recently, however, Becton, Dickinson and Company has demonstrated a CGM based on a fluorescently labeled glucose binding protein (GBP) contained in a glucose-permeable hydrogel matrix. The glucose binding protein undergoes a conformational change in the presence of glucose, which affects the fluorescence intensity. Accordingly fluorescence emission spectra may be used to determine glucose concentration continuously. One difficulty with fluorescence measuring systems is due to the inherently noisy nature of optical intensity signals. Another problem with CGM devices is with initial calibration, and maintaining calibration over the life of the sensor, to ensure accurate glucose measurements. Accordingly, there is a need for a CGM that is capable of self-calibration and dynamic calibration during use, in order to improve the speed and accuracy of glucose measurements. Although embodiments described herein discuss a GBP contained in a matrix, it should be appreciated that any suitable substance or compound may be contained within the matrix. Embodiments of the present invention are not limited to matrices containing a GBP, and in particular, may include without limitation boronic acid or any glucose binding compound. In addition, it should be understood that embodiments of the present invention may be deployed to any suitable location of a host, including without limitation subcutaneous, intradermal, supradermal, and intravascular space. Further, it should be understood that embodiments of the present invention may be deployed within or utilizing any bodily fluid, including without limitation, blood, urine, interstitial fluid, lymph fluid and tears.

SUMMARY OF THE INVENTION

Exemplary embodiments of the present invention address at least the above described problems and/or disadvantages and provide at least the advantages described below. Accordingly, it is an object of certain embodiments of the present invention to provide an optical analyte sensor for determining a concentration of an analyte. The sensor comprises a matrix for receiving a sample containing the analyte at an unknown concentration. The sensor comprises a light emitted for emitting light at a stimulation frequency upon the sample. A light receiver receives a fluorescence signal at a first isosbestic frequency, and at a second frequency, for measuring an intensity of the fluorescence signal at the first and second frequency. A processor determines a concentration of the analyte based on the respective intensities measured at the first and second frequencies.

Another exemplary embodiment of the invention provides a diabetes management system comprising an optical analyte sensor and an insulin infusion device. The optical analyte sensor comprises a matrix for receiving a sample containing the analyte at an unknown concentration and a light emitter for emitting light at a stimulation frequency upon the sample. The sensor further comprises a light receiver for receiving a fluorescence signal at a first isosbestic frequency, and at a second frequency, and for measuring an intensity of the fluorescence signal at the first and second frequencies. A processor determines a concentration of the analyte based on the respective intensities measured at the first and second frequencies. The sensor further comprises a transceiver for transmitting a signal to the insulin infusion device.

Yet another exemplary embodiment of the present invention provides an optical analyte sensor. The sensor comprises a matrix for receiving a sample containing the analyte at an unknown concentration and a light emitter for emitting light at a stimulation frequency upon the sample. The sensor further comprises a light receiver for receiving a fluorescence signal at a first isosbestic frequency, and at a second frequency, and for measuring an intensity of the fluorescence signal at the first and second frequencies. A processor determines a concentration of the analyte based on the respective intensities measured at the first and second frequencies. The processor further determines a sensor drift based on previous intensity measurements and corrects the determined concentration based on the determined sensor drift.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which.

Throughout the drawings, like reference numerals will be understood to refer to like elements, features and structures.

DETAILED DESCRIPTION OF EXEMPLARY EMBODIMENTS

Figure 1:
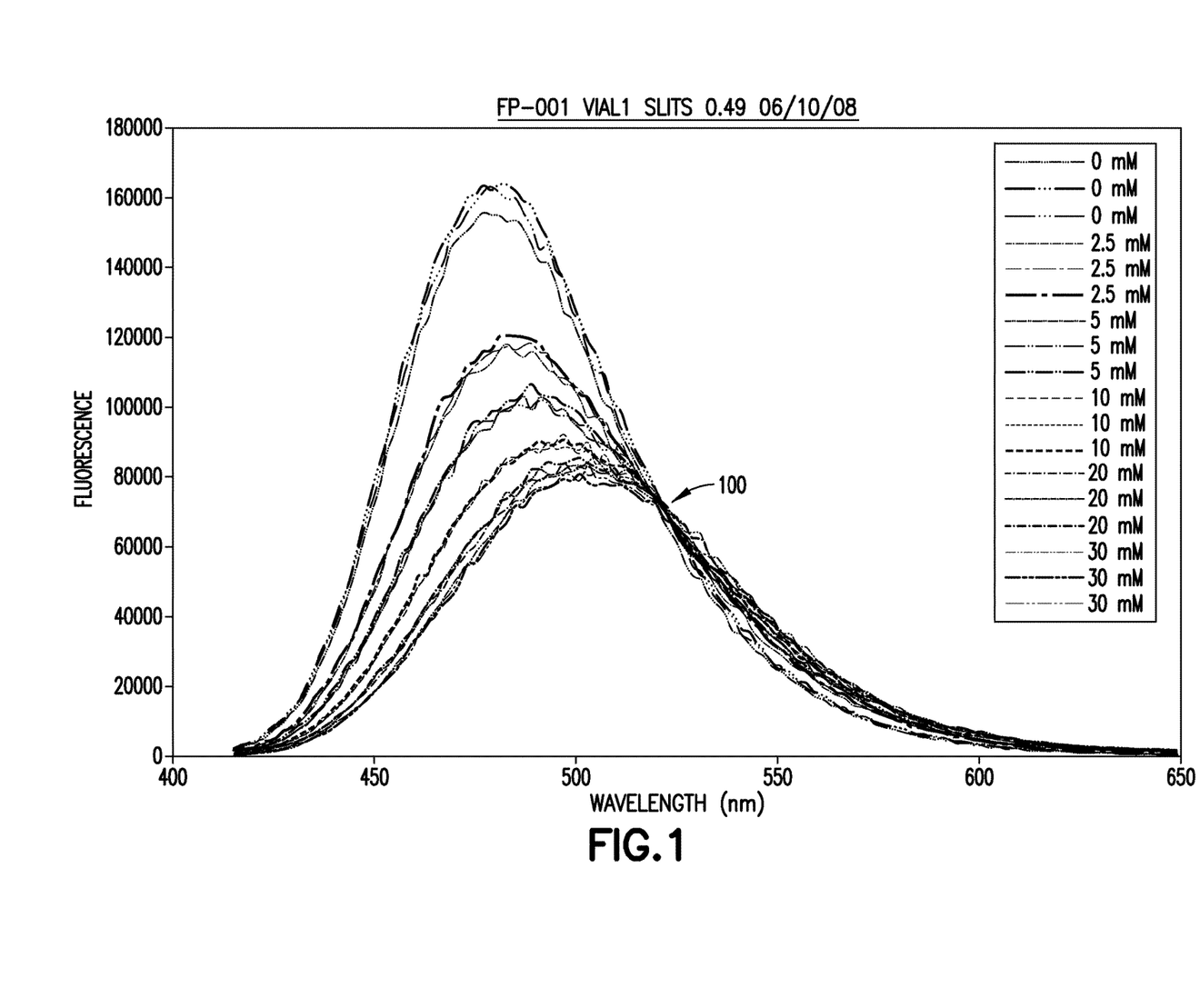
FIG. 1 illustrates a frequency response for a labeled GBP-based continuous glucose sensor having an isosbestic point according to an exemplary embodiment of the present invention.

Described herein is a novel system and method for estimating analyte concentration based on an invariant point in the fluorescence spectra of the GBP-acrylodan complex. A desirable analyte to measure is glucose, however, it should be appreciated that embodiments of the present invention can estimate the concentration of many different analytes including without limitation hemoglobin HbA1c and glycated albumin. An 'isosbestic' point typically refers to either an absorption or emission phenomena. Accordingly, the term 'isosbestic' as used herein refers to the analyte-invariant frequency of an emission spectra. As shown in FIG. 1, the frequency response for a labeled GBP-based continuous glucose sensor includes an isosbestic point 100. That is, there is a frequency for which intensity response is independent of the concentration of the target analyte. The isosbestic point is at approximately 520 nm.

The isosbestic point has been used to measure sensor performance independent of analyte concentration. This point and the range immediately around it may advantageously be used to dynamically self-reference the device and provide robust estimations of glucose levels. This approach enables a device that can be self-calibrated, and dynamically re-calibrated. An algorithm is provided that is based on physical models, and allows for more robust design and efficient risk management. Calculation of the estimated glucose concentration may advantageously be performed directly at any point in time, rather than relying on iterative and cumulative correction factors that are subject to drift and corruption.

In order for an isosbestic point to be present from an analyte-specific marker, such as a fluorescently-labeled GBP that enables detection of glucose, two and only two conformations of the marker need to exist. One conformation in the presence of the analyte to be measured and one conformation in the absence of that analyte. For example, one GBP used by Becton, Dickinson and Company contains a hinged point around which an open and closed GBP conformation exists. R. M. de Lorimier, J. J. Smith, M. A. Dwyer, L. L. Looger, K. M. Sali, C. D. Paavola, S. S. Rizk, S. Sadigov, D. W. Conrad, L. Loew, and H. W. Hellinga; *Construction of a fluorescent biosensor family*; Protein Science, (11):2655-2675, 2002. J. C. Pickup, F. Khan, Z.-L. Zhi, J. Coulter, and D. J. S. Birch; *Fluorescence intensity- and lifetime-based glucose sensing using glucose/galactose-binding protein*; J Diabetes Sci. Technol., 7(1):62-71, January 2013. K. Weidemaier, A. Lastovich, S. Keith, J. B. Pitner, M. Sistare, R. Jacobson, and D. Kurisko; *Multi-day pre-clinical demonstration of glucose/galactose binding protein-based fiber optic sensor*; Biosensors and Bioelectronics, (26):4117-4123, 2011.

A top-down, event-driven model has been derived. The model is simple and accurate. Simplicity enables ease of analysis, clarity in implementation, and reduces the risk of unintended effects due to unnecessary complexity. The model was derived according to the following process. First, initial assumptions were made based on reasonable evidence. Second, an analytical framework was developed that enables the calculation of an estimated glucose concentration inside the sensor. Third, a process was outlined to implement the findings in a commercial product. Fourth, experiments were conducted to collect and analyze data in order to support and/or refine the model, implementation, or process as needed.

A glucose value is converted to a measured signal through a number of process steps, outlined below. The algorithm reverses these steps so that the original glucose concentration in the sensor may be estimated accurately from the signal(s) measured by the device. The illustrative sequence of sensing events is as follows:

1. Glucose enters the sensor;
2. Glucose diffuses through the sensor;
3. Diffusion equilibrium is achieved;
4. Glucose molecules bind to glucose-binding protein molecules (GBP);
5. Bind modifies the fluorescence spectrum;
6. Binding equilibrium is achieved;
7. Light stimulates GBP;
8. GBP fluoresces; and
9. Fluorescence signal leaves sensor and is detected.

In the above process, diffusion, binding, equilibrium, and fluorescence are concurrent processes. To compute the signal, the sequence is reversed as follows:

1. Detect fluorescence signal;
2. Normalize signal;
3. Determine spectral signature of light;
4. Determine fractional concentration of emission states that create signature; and
5. Determine concentration of glucose that induces fractional concentration states.

The following definitions will be used in the subsequent discussion of an algorithm for determining glucose concentration.

Configuration Spectra:

$$\sigma_{open}(\lambda)=\sigma_{open}(\lambda,[G]=0)$$

$$\sigma_{closed}(\lambda)=\sigma_{closed}(\lambda,[G]=[G]_{saturated}\cong[G=\infty])$$

where $\lambda$ is the optical wavelength, $\sigma$ is the spectral density, [G] is the measured glucose concentration inside the sensor, and $[G]_{saturated}$ indicates the glucose concentration that will saturate GBP inside the sensor.

Optical Filters:

$$H_{ref}(\lambda) = \prod_{i \in ref\ path} H_i(\lambda)$$

$$H_{sig}(\lambda) = \prod_{i \in sig\ path} H_i(\lambda)$$

where $H_{ref}$ and $H_{sig}$ denote the net optical passbands, $H(\lambda)$, of the desired reference and signal channels, respectively. This includes the actual channel filters as well as any filters common to both channels, such as light source, autofluorescence, reflector, and detector transfer functions.

Fractional Saturation:

$Y \in [0,1]$ = fraction of GBP molecules saturated with glucose

The theory and derivations of the preferred algorithms for determining glucose concentration according to an exemplary embodiment of the present invention will now be discussed. One assumption is that the system is substantially in steady-state, meaning the system is substantially in diffusion equilibrium, chemical (binding) equilibrium, and thermal equilibrium. It should be noted that GBP operates as a two-state system, where:

$$n_{open} + n_{closed} = N$$

such that n is the number of GBP in their respective configurations and N is the number of active GBP in any configuration.

There is a crossing point in the fluorescence spectra of GBP, as shown in FIG. 1, represented by:

$$\exists \lambda = \lambda_{crossing} \in \Lambda \,\bigg|\, \sigma_{closed}(\lambda) \gg 0 \,\bigwedge\, \frac{d\sigma_{open}}{d\lambda} \neq \frac{d\sigma_{closed}}{d\lambda}$$

where $\Lambda$ is the optical wavelength range present in the system and $\sigma(\lambda) \gg 0$ is fulfilled when the amplitude of the crossing is sufficiently about the noise level, $s_{noise}$ to be accurately measured:

$$SNR_{dB} = 20\log_{10}\left(\frac{\sigma(\lambda_{crossing})}{s_{noise}}\right) \gg SNR_{dB,min}$$

The temperature range is preferably below protein denaturation and melting points. The atomic spectra of the base configurations, $\sigma_{open}(\lambda)$ and $\sigma_{closed}(\lambda)$, are substantially independent of temperature in the physiological range:

$$\frac{d\sigma(\lambda)}{dT} \simeq 0,\ T \in \text{physiological range}$$

Figure 2:
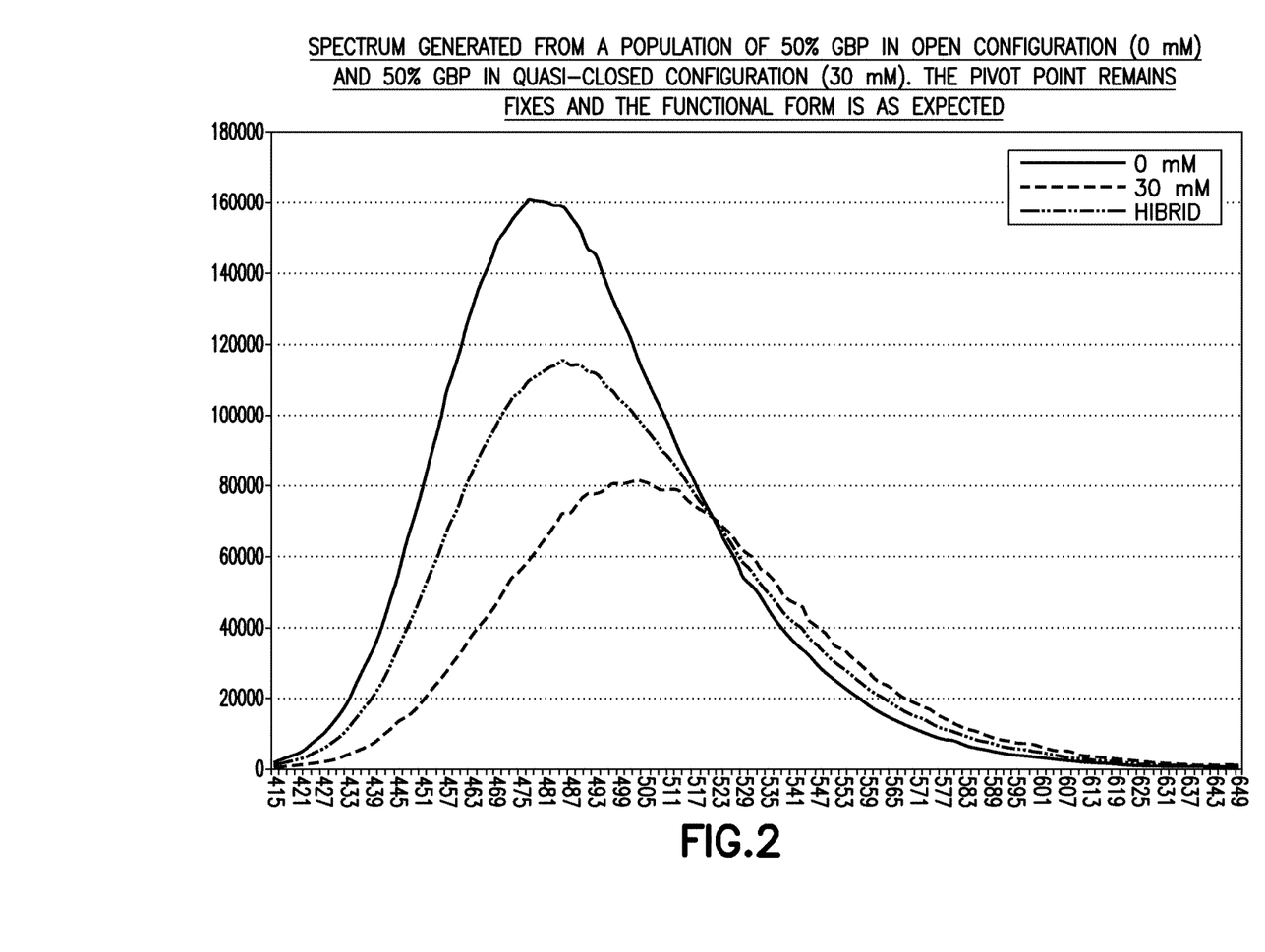
FIG. 2 illustrates a wavelength at which the spectral density is substantially independent of glucose concentration according to an exemplary embodiment of the present invention.

Due to the discrete, finite number of binding states and based on the observed spectra for open and closed configurations of GBP, there is a wavelength at which the spectral density is substantially independent of glucose concentration, as shown in FIG. 2.

A system comprised of N elements, each in one of C configurations, so that there are $n_i$ elements per configuration i, is represented by:

$$\sum_{i=1}^{c} n_i = N$$

Each configuration has an optical emission spectral density ('spectrum') associated with it:

$$\sigma_i(\lambda),\ i \in \{1 \ldots C\}$$

Assuming that system elements do not emit coherently, the amplitudes and intensities are additive, such that:

$$I_{system} = \sum_{j=1}^{N} I_j = \sum_{i=1}^{c} n_i \sigma_i$$

where $I_\# := n_\# \sigma_\#$ is the intensity emitted by all elements in state # with spectrum $\sigma_\#$.

Combining equations, the spectrum of the system, $\sigma_{system}$, is a weighted average of each of the constituent spectra:

$$\sigma_{system} = \frac{1}{N}\sum_{i=1}^{c} n_i \sigma_i$$

If there is a wavelength, $\lambda_{crossing}$, at which spectrum emitted by each configuration have the same amplitude:

$$\{\lambda_{crossing} | \sigma_i(\lambda_{crossing}) = \sigma_j(\lambda_{crossing})\}\ \forall i, j \in \{1 \ldots C\}$$

then it follows that:

$$\sigma_{crossing}(\lambda_{crossing}) = \frac{1}{N}\sum_{j=1}^{N} \sigma_j(\lambda_{crossing})$$

$$= \frac{1}{N}\sum_{i=1}^{c} n_i \sigma_i(\lambda_{crossing})$$

$$= \sigma_i(\lambda_{crossing})\frac{1}{N}\sum_{i=1}^{c} n_i$$

and since: $\frac{1}{N}\sum_{i=1}^{c} n_i = 1$ $$= \sigma_i(\lambda_{crossing})$$

Accordingly, there exists a wavelength, $\lambda_{crossing}$, at which the emitted light intensity is invariant with respect to glucose concentration:

$$\sigma(\lambda_{crossing}) \neq \sigma(\lambda_{crossing},[G])$$

Based on the equations above, there is a range of wavelengths, $\Lambda_{ref}$, such that the intensity is essentially invariant with respect to glucose, and therefore a reference intensity, $I_{ref}$:

$$|I_{ref} - \chi| = |\int_{\Lambda_{ref}} \sigma(\lambda,[G])d\lambda - \chi| < \varepsilon,\ \Lambda_{ref} \ni \lambda_{crossing},\ \varepsilon > 0,$$
$$\forall [G]$$

where $\chi$ is the measured intensity at [G]=0 in a band around the crossing point and $\varepsilon$ is an acceptable error term.

As GBP is one of two states, $n_{open}$ and $n_{closed}$, the spectrum emitted by the system is a weighted average of its component spectra:

$$\sigma_{system}(\lambda) = \frac{n_{open}\sigma_{open}(\lambda) + n_{closed}\sigma_{closed}(\lambda)}{n_{open} + n_{closed}}$$
$$= Y\sigma_{closed}(\lambda) + (1-Y)\sigma_{open}(\lambda)$$

where Y is the fractional concentration of bound emission states:

$$Y := \frac{n_{closed}}{n_{open} + n_{closed}}$$

The measured signal, I, is the power of the fluorescence spectrum over the detection range:

$$I = \int_\Lambda \sigma(\lambda)\lambda^{-2} d\lambda$$

Because the integration operator is linear and intensities are additive for incoherent light, the total power of the fluorescence spectrum can be represented by:

$$I_{total} = \int \sigma_{total}(\lambda)\lambda^{-2}d\lambda$$
$$= Y\int \sigma_{closed}(\lambda)\lambda^{-2}d\lambda + (1-Y)\int \sigma_{open}(\lambda)\lambda^{-2}d\lambda$$
$$= Y\left[\int \sigma_{closed}(\lambda)\lambda^{-2}d\lambda - \int \sigma_{open}(\lambda)\lambda^{-2}d\lambda + (1-Y)\right] +$$
$$\int \sigma_{open}(\lambda)\lambda^{-2}d\lambda$$
$$= Y\left[\int (\sigma_{closed}(\lambda) - \sigma_{open}(\lambda))\lambda^{-2}d\lambda\right] + \int \sigma_{open}(\lambda)\lambda^{-2}d\lambda$$

If $\Lambda$ is constrained to the signal range, $\Lambda = \Lambda_{sig}$, then solving the above equation for Y provides:

$$Y = \frac{\int_{\Lambda_{sig}} \sigma_{total}(\lambda)\lambda^{-2}d\lambda - \int_{\Lambda_{sig}} \sigma_{open}(\lambda)\lambda^{-2}d\lambda}{\int_{\Lambda_{sig}} (\sigma_{closed}(\lambda) - \sigma_{open}(\lambda))\lambda^{-2}d\lambda}$$

The detected spectra, $\sigma_{sig}(\lambda)$ and $\sigma_{ref}(\lambda)$, are functions of the optical filters, $H_{sig}$ and $H_{ref}$ along with the signal and reference paths, respectively.

$$\sigma_{sig}(\lambda) = H_{sig}(\lambda) \cdot \sigma_{total}(\lambda)\lambda^{-2}d\lambda$$

$$\sigma_{ref}(\lambda) = H_{ref}(\lambda) \cdot \sigma_{total}(\lambda)\lambda^{-2}d\lambda$$

Therefore, the measured light intensities, $$I_{sig} = \int_\Lambda H_{sig}(\lambda) \cdot \sigma_{total}(\lambda)\lambda^{-2}d\lambda$$

$$I_{ref} = \int_\Lambda H_{ref}(\lambda) \cdot \sigma_{total}(\lambda)\lambda^{-2}d\lambda$$

As discussed above, the reference signal is independent of the glucose concentration [G]. Therefore, it can be used as a normalization factor for all spectral and intensity calculations. This, in turn, allows for direct comparison and use of any spectra from any device at any time, provided that the fluorescence characteristics of the base states, $\sigma_{open}$ and $\sigma_{closed}$, have not been altered. Therefore, all measurements of $I_{sig}$ will be normalized by the concurrently measured value of $I_{ref}$.

The values $\sigma_{open}$, $\sigma_{closed}$, $H_{sig}$, and $H_{ref}$ are able to be characterized and recorded prior to deployment of a sensor according to an exemplary embodiment of the present invention. Thus, using the tilde (e.g., $\tilde{\sigma}_{open}$) to denote recorded values, combining the equations above, and normalizing to $I_{ref}$ yields:

$$Y = \frac{I_{sig} \cdot \frac{1}{I_{ref}} \cdot \int_\Lambda \tilde{H}_{ref}(\lambda)\tilde{\sigma}_{open}(\lambda)\lambda^{-2}d\lambda - \int_\Lambda \tilde{H}_{sig}(\lambda)\tilde{\sigma}_{open}(\lambda)\lambda^{-2}d\lambda}{\int_\Lambda (\tilde{H}_{sig}(\lambda)\tilde{\sigma}_{closed}(\lambda) - \tilde{H}_{sig}(\lambda)\tilde{\sigma}_{open}(\lambda))\lambda^{-2}d\lambda}$$

where $\Lambda$ denotes the range of wavelengths in the system.

The above equation determines the fractional concentration of base states. It also advantageously corrects the previously measured full spectra of the base states, $\tilde{\sigma}$-open and to match the actual spectra in the device by applying the previously measured characteristics of the optical filters assembled in the device, $\tilde{H}_{sig}$ and $\tilde{H}_{ref}$. For example, $$\sigma_{sig,open,device} = \tilde{H}_{sig}(\lambda)\tilde{\sigma}_{open}(\lambda)$$

is the effective spectrum of the open base state that is incident on the signal channel of the device.

The above equation also calculates the power incident on the photodetectors by numerically integrating the spectrum over the range of wavelengths:

$$\int_\Lambda \tilde{H}_{sig}(\lambda)\tilde{\sigma}_{open}(\lambda)\lambda^{-2}d\lambda$$

This is the power that would be measured by the signal detector if all emitters were in the open state. The previously measured invariant reference is then computed for the previously measured spectra in a similar manner to above:

$$\int_\Lambda \tilde{H}_{ref}(\lambda)\tilde{\sigma}_{open}(\lambda)\lambda^{-2}d\lambda$$

The reference, $I_{ref}$, and the signal, $I_{sig}$, are acquired from the device and the signal is normalized so that all spectra in the equation are based on the same factory-measured reference.

$$I_{sig} \cdot \left\{\frac{1}{I_{ref}} \cdot \int_\Lambda \tilde{H}_{ref}(\lambda)\tilde{\sigma}_{open}(\lambda)\lambda^{-2}d\lambda\right\}$$

The next step is to determine how the presence of glucose affects the fractional concentration of emitters, that is, how glucose concentration drives the equilibrium between the states. In the case of simple binding of a ligand, G, to a protein, P, $$P + G \rightleftharpoons P{:}G$$

the dissociation constant, $K_D$, is given by $$K_D = \frac{[P][G]}{[P{:}G]}$$

Conversely, the equilibrium constant (also known as the association constant or affinity, $K_A$), $K_{eq}$, is given by $$K_{eq} = \frac{1}{K_D} = \frac{[P{:}G]}{[P][G]}$$

In the case of one GBP binding one glucose molecule, the fractional saturation, Y, is the ratio of the moles of glucose bound to the moles of protein:

$$Y = \frac{[P{:}G]}{[P] + [P{:}G]}$$

which, by substituting and simplifying, results in:

$$Y = \frac{[G]}{K_D + [G]} = \frac{n_{closed}}{n_{closed} + n_{open}}$$

By further combining equations and solving for [G], the following equation that solves for glucose concentration is obtained:

$$[G] = K_D \cdot \left[ \frac{I_{ref} \cdot \int_\Lambda (\tilde{H}_{sig}(\lambda)\tilde{\sigma}_{closed}(\lambda) - \tilde{H}_{sig}(\lambda)\tilde{\sigma}_{open}(\lambda))\lambda^{-2} d\lambda}{I_{sig} \cdot \int_\Lambda \tilde{H}_{ref}(\lambda)\tilde{\sigma}_{open}(\lambda)\lambda^{-2} d\lambda - \int_\Lambda \tilde{H}_{sig}(\lambda)\tilde{\sigma}_{open}(\lambda)\lambda^{-2} d\lambda} - 1 \right]^{-1}$$

The above equation is a hyperbolic function of the normalized signal intensity and a linear function of the dissociation constant, $K_D$.

The optical filters and their transfer functions, $H(\lambda)$, are preferably characterized prior to use. As the signal and reference filters, $H_{sig}$ and $H_{ref}$, are defined as the net filters on that signal path, they are preferably measured in conjunction with any common filters and transfer functions in the system, that is, light source filter, detector filter, beam splitting dichroic, or spectra-altering reflective coatings. Characterization is preferably performed over wavelengths from approximately 380 nm to approximately 700 nm in steps of, for example, 1 nm. Components are measured with the light incident on them at angles equal to those used in the device. Several spectra are preferably measured for each base state in order to ensure stability and accuracy of measurements. The final functions, $H(\lambda)$, are preferably stored for each of the components in each OBS that uses that specific lot in its sensor.

Reference Band

Because real world filters cannot isolate a single frequency, it is preferable to find a quasi-invariant reference band. This can be represented as:

$$|\int_\Lambda H_{ref}(\lambda)\sigma_{open}(\lambda)\lambda^{-2}d\lambda - \int_\Lambda H_{ref}(\lambda)\sigma_{closed}(\lambda)\lambda^{-2}d\lambda| < \varepsilon;$$
$$\varepsilon > 0$$

where $\varepsilon$ is determined by the acceptable variation on the reference channel.

As discussed above, there is a crossing in the base spectra. Thus the contribution of each configuration to the intensity measured in the reference channel, $I_{ref}$, is reversed about the crossing point, $\lambda_{crossing}$. As the weighted average, $\sigma_{total}$, changes from $\sigma_{open}$ to $\sigma_{closed}$, the contribution of $I_{ref}$ will be monotonically decreasing in the range $\lambda < \lambda_{crossing}$ and monotonically increasing in the range $\lambda > \lambda_{crossing}$. Accordingly, by virtue of the additivity of optical intensities and the linearity of the intergration operator, if there is a range $[\lambda_{ref,min}; \lambda_{ref,max}]$, such that $$\int_{\lambda_{ref,min}}^{\lambda_{ref,max}} \sigma_{open}(\lambda)\lambda^{-2} d\lambda = \int_{\lambda_{ref,min}}^{\lambda_{ref,max}} \sigma_{closed}(\lambda)\lambda^{-2} d\lambda := \Re$$

then the intensity measured over this range will be the same for all mixed configurations, that is, independent of the glucose concentration in the sensor. In other words, as all spectra are a linear combination of the base spectra, and as integration (power) is linear, it is only necessary to find the largest range that is maximally invariant between the two base states. As the detected power increases with a broader detection range, the goal is to find as broad a passband as possible that meets the condition stated in the above equation, as this will maximize the total detected power and increase the SNR of the reference channel. This will also mitigate issued related to the numerical stability of dividing by a small number.

Referring to the data presented in FIG. 2, an optimal passband range was determined to be from approximately 497 nm to approximately 617 nm.

$$\int_{497\,nm}^{617\,nm} \sigma_{open}(\lambda)\lambda^{-2} d\lambda = \int_{497\,nm}^{617\,nm} \sigma_{closed}(\lambda)\lambda^{-2} d\lambda := \Re \neq \Re[G]$$

Using the preliminary data presented in FIG. 2, the difference between the reference signals from each of the two base states was:

$$\frac{|I_{ref,open} - I_{ref,closed}|}{I_{ref,open}} = \frac{|2{,}240{,}235 - 2{,}240{,}267|}{2{,}240{,}235}$$
$$= \frac{31.5}{2{,}240{,}235}$$
$$= 0.0014\%$$
$$\simeq 0$$

The level of variance found above is small enough to be considered practically invariant with respect to glucose concentrations.

Signal Band

It is preferable to find a passband to use as the signal channel that will maximize the total detected power and increase SNR. The signal channel is also preferably maximally sensitive to any change in glucose. Because, as discussed above, all spectra are a linear combination of the base spectra, and as integration (power) is additive, it is only necessary to find the largest range that is maximally changing between the two base states.

$$|\int_\Lambda H_{sig}(\lambda)\sigma_{open}(\lambda)\lambda^{-2}d\lambda - \int_\Lambda H_{sig}(\lambda)\sigma_{closed}(\lambda)\lambda^{-2}d\lambda|$$
maximized The data presented in FIG. 2 may be used to estimate this range. The optimal signal band was found to range from 415 nm, that is, the lowest wavelength available to the signal detector, to 521 nm=$\lambda_{crossing}$, that is, the highest wavelength before the spectra reverse and changes in concentration begin to cancel each other out. The lower edge of the passband is determined by the longest wavelength from the excitation source that is allowed to enter the system in non-negligible amounts. Using preliminary data, the difference between the reference signals from each of the two base states was:

$$\frac{|I_{ref,open} - I_{ref,closed}|}{I_{ref,open}} = \frac{|4,928,890 - 2,315,596|}{4,928,890}$$

$$= \frac{2,613,294}{4,928,890}$$

$$= 53\%$$

A series of graphs generated from the experimental set of spectra presented in FIG. 1 will now be described. Each spectrum was acquired three times for each concentration level and averaged. The 0 mM glucose and 30 mM glucose (not fully saturated, but the highest concentration available for the analysis) were then integrated over all filter range combinations from 415 nm to 649 nm. Filters were assumed to be ideal, that is:

$$\begin{cases} H(\lambda) = 0, & \lambda < \text{lower limit} \\ H(\lambda) = 1, & \text{lower limit} \leq \lambda \leq \text{upper limit} \\ H(\lambda) = 0, & \lambda > \text{upper limit} \end{cases}$$

Figure 3:
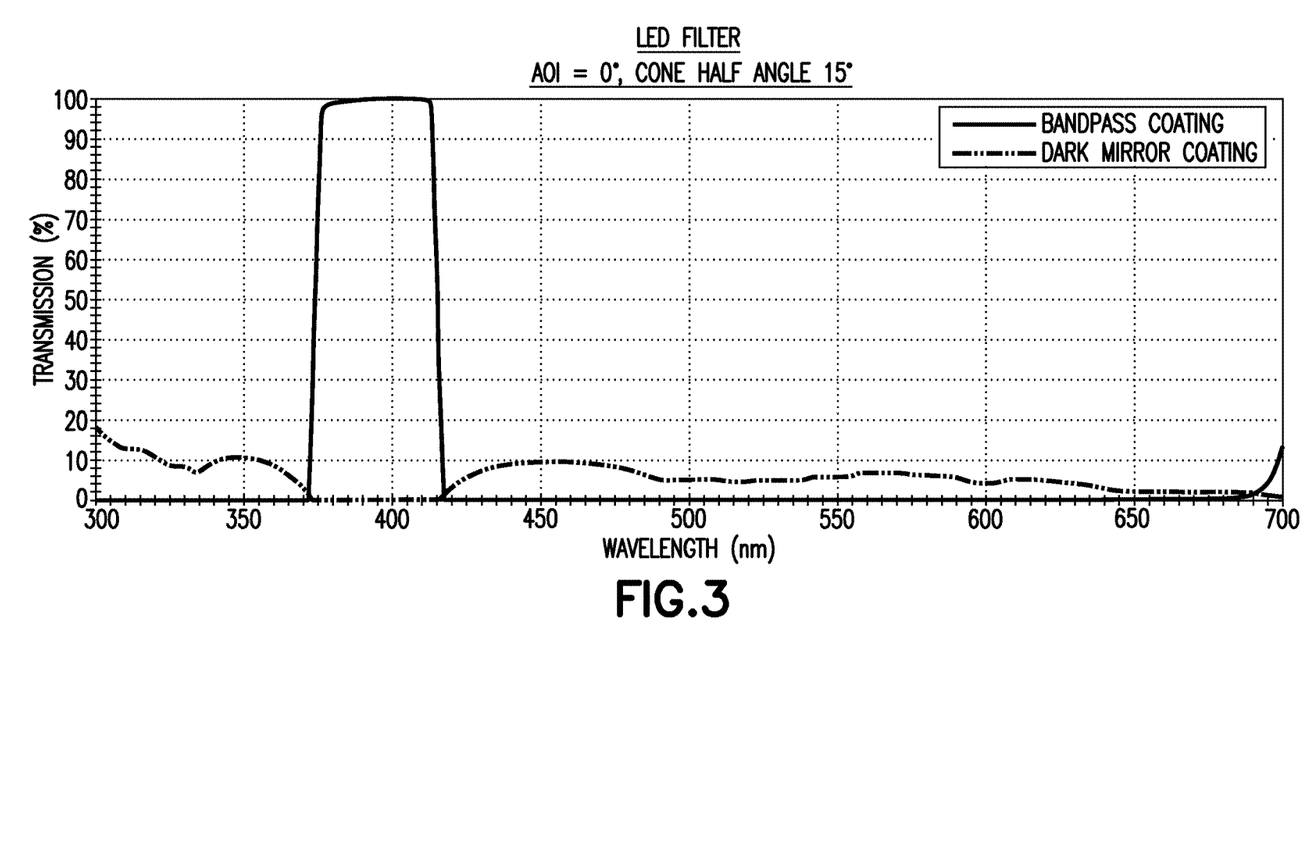
FIG. 3 illustrates a comparison between an idealized filter and a real optical filter model according to an exemplary embodiment of the present invention.

A comparison of this idealized filter with an actual optical filter model is shown in FIG. 3. The change in signal from 0 mM to 30 mM was then computed for each filter range by calculating the absolute difference between the intensities at each of the two base concentrations. The optimal signal channel, $H_{sig}$, will show the largest change in signal over the range of concentrations. The optimal reference channel, $H_{ref}$, will show negligible change over the range of concentrations. The optimal signal range was found to be from 415 nm to 521 nm and is limited at the low end by the emission spectrum of the light source. The optimal reference range was found to be from 497 nm to 617 nm.

Figure 4:
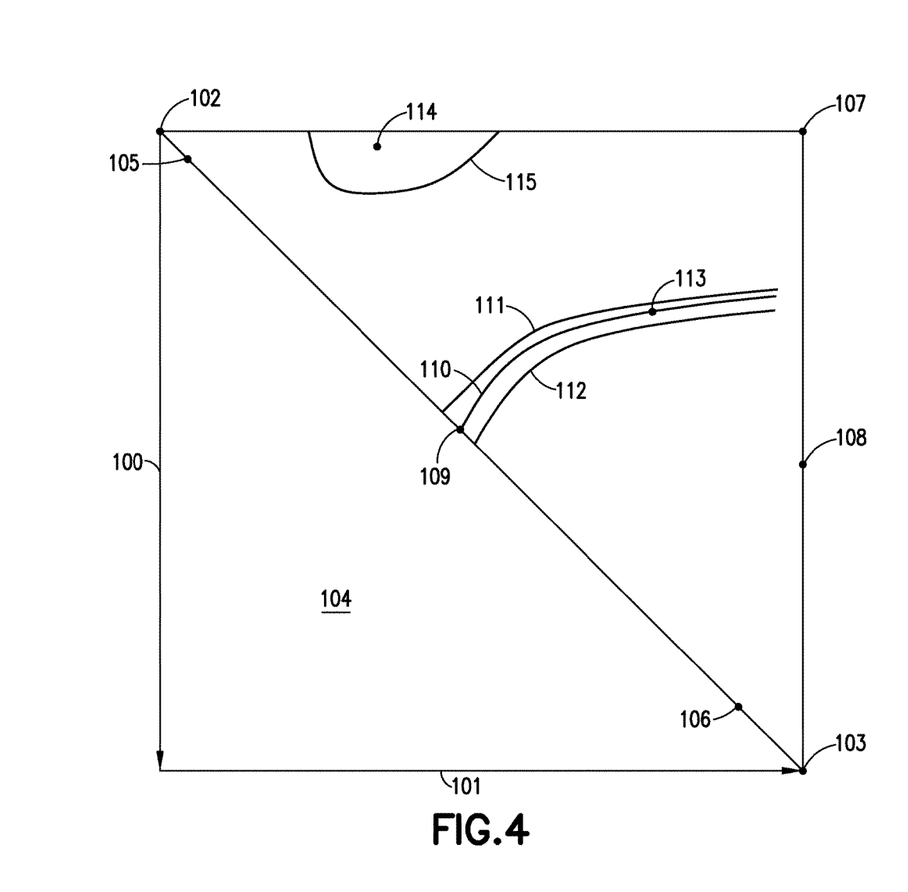
FIG. 4 illustrates the change in measured signal strength intensity between two states of interest as a function of detection passband configurations according to an exemplary embodiment of the present invention.

FIG. 4 illustrates the change in measured signal strength intensity between two states of interest as a function of detection passband configurations. An invariant passband which is suitable for use in real-time calibration will exhibit negligible or no change with analyte concentration. A strong signal will exhibit a large change with analyte concentration. During the design and fabrication of the measurement device, the optimal passbands are determined for both the reference and the signal channels. While in use, the signal is first treated ratiometrically by dividing the signal intensity by the substantially invariant reference intensity. This ratiometric operation is performed to normalize all signals to the reference signal, thereby ensuring that all signals are interpreted on the same scale and in the same units across devices and over the use of any single device. The normalized signal then serves as the basis for real-time calibration of the device. In exemplary embodiments of the invention, all three steps consisting of ratiometric measurement, normalization, and calibration are performed simultaneously in one operation. This is substantially different from conventional techniques whereby only some of the steps are performed, and preventing real-time calibration, or additional steps are added at a later stage to attempt calibration.

In FIG. 4, the axis representing the lower limit of an optical passband is shown at 100. The axis 100 spans the range of wavelengths of interest in the system. The orientation of the axis is denoted by the vertical arrow in the frame. The axis representing the upper limit of an optical passband is illustrated at 101. The axis 101 spans the range of wavelengths of interest in the system. The orientation of the axis 101 is denoted by the horizontal arrow in the frame.

The lower end 102 of the range of interest denotes the minima of axes 100 and 102. The upper end 103 of the range of interest denotes the maxima of axes 100 and 102. In area 104, the lower limits are greater than the upper limits, and are therefore not applicable, so this area is blank. Example 105 is a narrow passband at the lower end of the range of interest. Example 106 is a narrow passband at the upper end of the range of interest. Example 107 is a passband that encompasses the entire range of interest. Example 108 is a passband that spans the upper half of the range of interest. Point 109 is the isosbestic or invariant point. Band 110 illustrates passbands that are invariant with respect to analyte concentration. Bands 111 and 112 are passbands that have variability with respect to analyte concentration but are sufficiently small to be considered essentially invariant. Example 113 is an example of a passband specification chosen for an embodiment as the calibration reference. Band 114 is a passband that exhibits maximal change with respect to analyte concentration. Area 115 delimits the range of passbands that have significant change with respect to analyte concentration. These have sufficiently large change to be considered optimal signal passbands.

Figure 5:
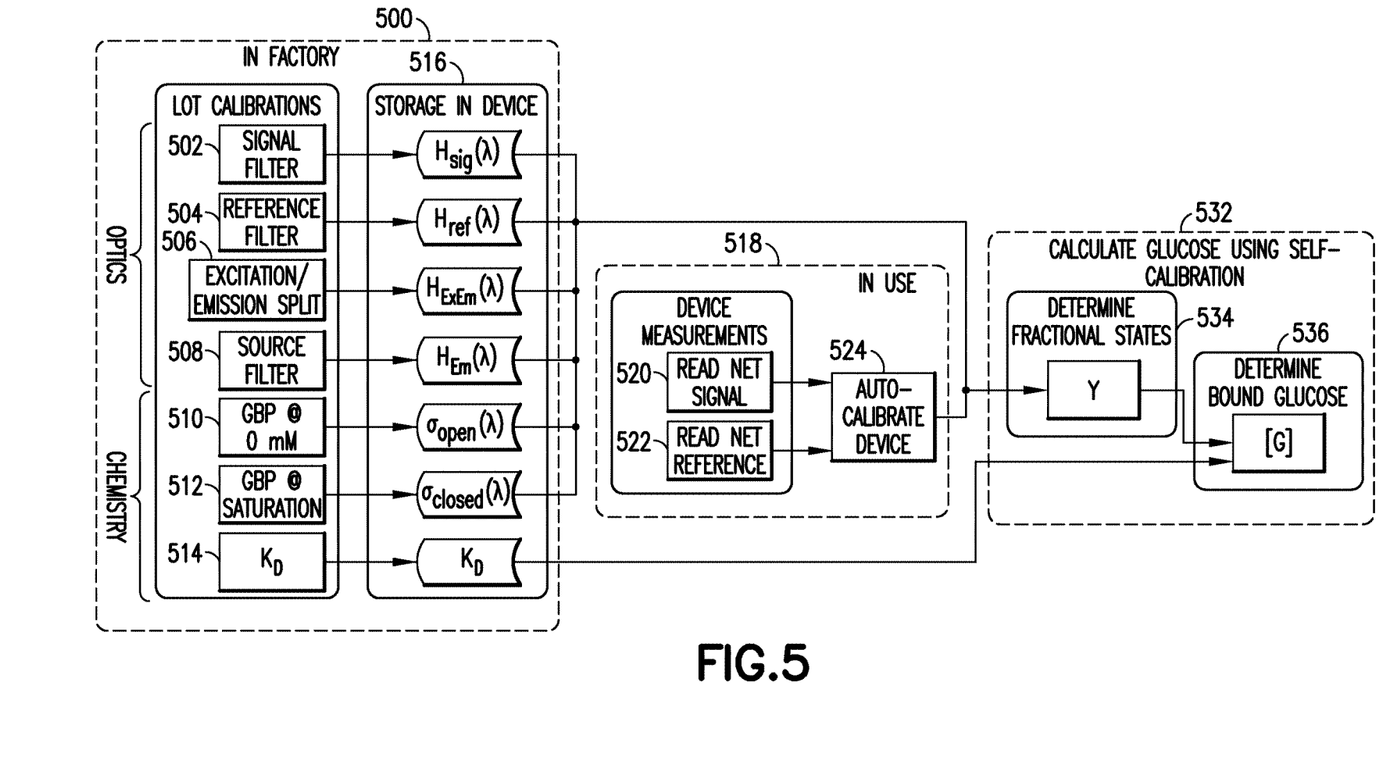
FIG. 5 illustrates a block diagram of a calibration process according to an exemplary embodiment of the present invention.

A process of lot calibration of selected components of a sensor according to exemplary embodiments of the present invention will now be described in connection with FIG. 5. As illustrated, various components related to the optics and chemistry of the device are preferably calibrated in lots at the factory or at the vendor. These components, shown in block 500, preferably include a signal filter 502, reference filter 504, excitation/emission split 506, source filter 508, GBP at 0 mM 510, GBP at saturation 512, and $K_D$ 514. Calibration parameters related to each are preferably stored in the device, as shown in block 516. As shown in block 518, in use the device reads a net signal 520 and net reference 522 and determines auto-calibration data 524 for the device based on the net signal 520 and net reference 522. Glucose concentration is determined using self calibration 532 with input from parameters stored in storage device 516 and auto-calibration data 524. Fractional states of GBP are determined at 534, and then bound glucose is determined from the fractional states and $K_D$ at 536. Lot calibration advantageously eliminates the extensive device-level calibration and accordingly supports high-throughput manufacturing. Calculations are preferably performed real-time while in use to estimate the glucose concentration inside the sensor.

Exemplary devices and methods for sensing glucose concentration described herein have significant advantages in performance, fabrication, and accuracy. Dynamic self-referencing to the invariant crossing point advantageously corrects for photobleaching, excitation light source variability (both nominal and drift), detector variation, coupling and alignment effects (including thermal), and optical filter variation. Accordingly, this approach offers an exact and dynamic calibration technology, which in turn produces a true self-referencing system.

The approach described herein guides and simplifies design, testing and calibration of a device. The approach also enables automated real-time calibration of the device in use.

Identifying optimal filter bands and storage of component characteristics inside the device, as described herein, enable more robust design. Indeed, much of the variability in the components can be characterized in lot testing and accounted for in the equations described above. This advantageously results in a simpler, more robust design that uses fewer tight tolerance components, fewer custom components, a simplified assembly process, and simplified testing.

Although only a few embodiments of the present invention have been described, the present invention is not limited to the described embodiment. Instead, it will be appreciated by those skilled in the art that changes may be made to these embodiments without departing from the principles and spirit of the invention.

What is claimed is:

1. An optical analyte sensor for determining a concentration of glucose, comprising:

a glucose permeable hydrogel matrix comprising a glucose binding protein (GBP) that adopts a first conformation in the presence of glucose, and a second conformation in the absence of glucose, the conformational change resulting in a different fluorescence emission intensity, the matrix adapted to receive a sample containing glucose at an unknown concentration;

wherein the GBP within the glucose permeable hydrogel matrix is adapted to fluoresce at an intensity invariant to the glucose concentration within the matrix at an isosbestic frequency when subjected to an excitation source, and to fluoresce at an intensity that varies according to glucose concentration at a second frequency when subjected to an excitation source;

a reference filter optically coupled to the matrix that passes a reference fluorescence emission from the matrix at a reference frequency, the reference frequency being an isosbestic frequency relative to the glucose binding protein, wherein the reference filter is a bandpass filter having an optimal bandpass range around the isosbestic frequency, a signal filter optically coupled to the matrix that passes a signal fluorescence emission from the matrix at a signal frequency, the signal frequency being an intensity variant frequency relative to the glucose binding protein, wherein the signal filter is a bandpass filter having a bandpass range selected to optimize detected power;

a photodetector to detect an intensity of the reference fluorescence emission and an intensity of the signal fluorescence emission; and a processor adapted to compare the fluorescence intensity of the reference fluorescence emission and the signal fluorescence emission, and to determine a glucose concentration based on the relative intensities.

2. The optical analyte sensor as claimed in claim 1, wherein the sensor is an in-vitro sensor.

3. The optical analyte sensor as claimed in claim 1, wherein the sensor is an in-vivo sensor.

4. The optical analyte sensor as claimed in claim 1, wherein the sensor is a continuous sensor.

5. The optical analyte sensor as claimed in claim 1, wherein the analyte is hemoglobin HbA1c.

6. The optical analyte sensor as claimed in claim 1, wherein the analyte is glycated albumin.

7. The optical analyte sensor as claimed in claim 1, wherein the matrix comprises boronic acid.

* * * * *